United States Patent
Parab et al.

(10) Patent No.: US 9,670,144 B2
(45) Date of Patent: Jun. 6, 2017

(54) PROCESS FOR THE PREPARATION OF 2-CYANO-3,3-DIARYLACRYLATES

(71) Applicant: GALAXY SURFACTANTS LTD., Navi Mumbai (IN)

(72) Inventors: Bharat Bhikaji Parab, Mumbai (IN); Rushit Ramakant Mhatre, Navi Mumbai (IN); Anchita Ravinder Tanwar, Navi Mumbai (IN); Archana Kishor Desai, Kurla (IN)

(73) Assignee: Galaxy Surfactants, Ltd., Maharashtra (IN)

( * ) Notice: Subject to any disclaimer, the term of this patent is extended or adjusted under 35 U.S.C. 154(b) by 0 days.

(21) Appl. No.: 14/787,568

(22) PCT Filed: Dec. 6, 2013

(86) PCT No.: PCT/IN2013/000753
§ 371 (c)(1),
(2) Date: Oct. 28, 2015

(87) PCT Pub. No.: WO2014/178061
PCT Pub. Date: Nov. 6, 2014

(65) Prior Publication Data
US 2016/0075640 A1    Mar. 17, 2016

(30) Foreign Application Priority Data

May 2, 2013 (IN) .......................... 1586/MUM/2013

(51) Int. Cl.
*C07C 253/30*   (2006.01)
*C07C 253/32*   (2006.01)

(52) U.S. Cl.
CPC .......... *C07C 253/30* (2013.01); *C07C 253/32* (2013.01)

(58) Field of Classification Search
CPC .................................................... C07C 253/30
See application file for complete search history.

(56) References Cited

U.S. PATENT DOCUMENTS

| 2,623,060 | A | | 12/1952 | Cragoe |
| 5,451,694 | A | * | 9/1995 | Kuhn .................... C07C 253/30 558/374 |
| 5,917,080 | A | | 6/1999 | Holderbaum et al. |
| 2011/0014140 | A1 | | 1/2011 | Huang et al. |

FOREIGN PATENT DOCUMENTS

| EP | 0430023 A1 | 6/1991 |
| WO | 2014178061 A2 | 11/2014 |

OTHER PUBLICATIONS

"International Search Report for PCT/IN2013/000753 dated Jan. 21, 2015".

* cited by examiner

*Primary Examiner* — Shawquia Jackson
(74) *Attorney, Agent, or Firm* — Kramer Amado, P.C.

(57) ABSTRACT

The present invention relates to a novel process for preparation of 2-Cyano-3,3-diarylacrylates by the Knoevenagel condensation of Cyanoacetic esters and Arylketones using ammonium compound and acetic acid and without the use of organic solvent.

14 Claims, No Drawings

_US 9,670,144 B2_

PROCESS FOR THE PREPARATION OF 2-CYANO-3,3-DIARYLACRYLATES

FIELD OF INVENTION

The present invention relates to a novel process for the preparation of 2-Cyano-3,3-diarylacrylates. In particular, the present invention relates to a cost effective preparation of 2-Cyano-3,3-diarylacrylates using acetic acid with a very good conversion and control of unwanted impurities.

BACKGROUND OF INVENTION

2-Cyano-3,3-diarylacrylates, with structural Formula I, is widely used in creams and lotions as a Sun protection factor (SPF) booster. The extended conjugation of the acrylate portion of the molecule absorbs UVB and short-wave UVA (ultraviolet) rays with wavelengths from 280 to 320 nm.

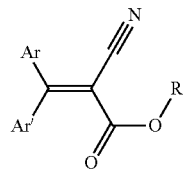

Formula I

2-Cyano-3,3-diarylacrylates are generally prepared by the Knoevenagel condensation of either 1) Cyanoacetic ester with Arylketone or 2) Alkyl cyanoacetate with Arylketone followed by transesterification with alcohol.

Compounds of Formula I were first disclosed in U.S. Pat. No. 3,215,725 wherein the process for preparation is also disclosed. This process involves reaction of Arylketone with ethylene glycol di-(☐-cyanoacetate) in the presence of ammonium acetate, glacial acetic acid in benzene. However, the drawback of this process is that the product formed is discolored and therefore the purification is extremely laborious.

U.S. Pat. No. 5,047,571 describes a process for preparation of 2-Cyano-3,3-diarylacrylates by transesterification with alcohol at 130° C. in presence of basic catalyst with continuous removal of resulting alcohol. The resulting product was purified by film evaporation process.

Most of the patents describe the use of organic solvents for the removal of water of reaction azeotropically. U.S. Pat. No. 2,623,060 discloses use of aromatic solvents for the removal of water of reaction azeotropically. U.S. Pat. Nos. 3,337,357, 3,544,466 and 4,207,523 disclose a general method for making substituted phenylcinnamates wherein the reactants are combined with an aromatic solvent and catalyst, heated to reflux, wherein water is removed and the product is recovered from the solvent. These patents generally give a yield of 60 percent to 70 percent product.

EP0430023 discloses the preparation of 2-Cyano-3,3-diarylacrylates by reaction of Arylketone with cyanoacetic acid ester in the presence of ammonium acetate and glacial acetic acid using heptane for the removal of water of reaction azeotropically. The process involves long reaction time and use of metering pump to add the catalyst periodically through the course of the reaction.

U.S. Pat. No. 5,451,694 discloses the process of making 2-Cyanocinnamic esters in organic solvent such as Propanoic acid. However, comparative example I conducted as per the process given in this patent, indicates significant generation of Biphenyl cyanoacrylamide (BPCA). Further, the process is not economical due to cost and availability of C3-C6 monocarboxylic acids.

Patent application 2831/MUM/2010 discloses the preparation of substituted Diphenylcyanoacrylate compounds using cyclohexane, hexane or toluene as solvent.

All the processes of the prior art require long reaction times for obtaining high yields, thereby leading to more formation of unwanted impurities like Diaryl cyanoacrylamide. Besides this, the use of aromatic solvent puts restriction on commercial proposition of these routes due to carcinogenicity of aromatic solvents, in addition to increase in the cost.

Hence, there is a need to develop an, efficient and industrially viable process for the preparation of 2-Cyano-3,3-diarylacrylates.

Accordingly it is an object of the present invention to provide a cost-effective process for the preparation of 2-Cyano-3,3-diarylacrylates from Arylketone and Cyanoacetic ester with high yields and good purity.

In achieving the above objective, the inventors of present invention have developed a process to obtain 2-Cyano-3,3-diarylacrylates using acetic acid and ammonium compound with very good control over the formation of Diaryl cyanoacrylamide (<0.2%) in reaction mass. Further, the process of the present invention does not involve any organic solvent for removal of water of reaction. The process is cost effective, operationally simple, exploits cheap and commercially available raw material, acetic acid, with very good conversion under reduced pressure with a control over impurities. Further the recovered acetic acid can be reused as such or after removal of water.

SUMMARY OF INVENTION

In accordance with the above objective, the present invention provides a cost-effective process for the preparation of 2-Cyano-3,3-diarylacrylates of Formula I

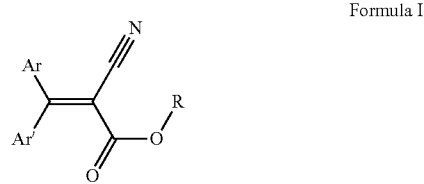

Formula I wherein,

Ar=Ar'=Phenyl or substituted phenyl

R=$C_1$-$C_{12}$ alkyl comprising, reacting Cyanoacetic ester of Formula II

Formula II with Arylketone of Formula III

Formula III in presence of ammonium compound and acetic acid and in the absence of organic solvent.

In particular, the present invention relates to an improved process for the preparation of 2-Cyano-3,3-diarylacrylates which includes reaction of Arylketone and Cyanoacetic ester in acetic acid with high yields and purity, wherein the reaction is devoid of use of any organic solvent.

In another aspect, the invention provides method of recycling of acetic acid for an efficient process for the preparation of 2-Cyano-3,3-diarylacrylates with very good control over the formation of Diaryl cyanoacrylamide (<0.2%), an impurity in reaction mass.

In a further aspect, the present invention provides a process for the preparation of 2-Ethylhexyl-3,3-biphenyl-cyanoacrylate from benzophenone and 2-Ethylhexyl cyano-acetate in acetic acid without using any organic solvent.

In yet another aspect, the invention provides a process for the preparation of Amyl-3,3-biphenylcyanoacrylate from benzophenone and amyl cyanoacetate in acetic acid without using any organic solvent.

DETAILED DESCRIPTION OF INVENTION

The invention will now be described in detail in connection with certain preferred and optional embodiments, so that various aspects thereof may be more fully understood and appreciated.

The present invention provides the novel and improved processes for the preparation of 2-Cyano-3,3-diarylacrylates of Formula I.

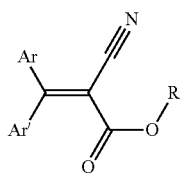

Formula I wherein,
Ar=Ar'=Phenyl or substituted phenyl
R=$C_1$-$C_{12}$ alkyl

According to an embodiment of the present invention, there is provided a cost-effective process for the preparation of 2-Cyano-3,3-diarylacrylates of Formula (I), which comprises, reacting Cyanoacetic ester of Formula II with Arylketone of Formula III in presence of ammonium compound and acetic acid, wherein the process is devoid of use of organic solvent.

The process of the present invention for preparation of 2-Cyano-3,3-diarylacrylates of Formula I is depicted in following Scheme 1.

SCHEME 1

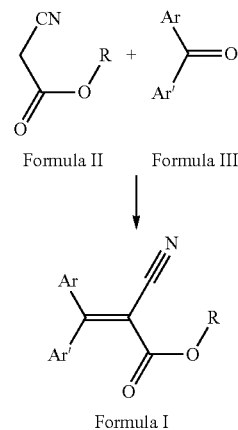

wherein,
Ar=Ar'=Phenyl or substituted phenyl
R=C1-C12 alkyl

According to another embodiment of the present invention, the ammonium compound is selected from ammonia or ammonium salts. One of the preferable ammonium salt is ammonium acetate. The amount of ammonium acetate used in the reaction is preferably 0.05-0.4 mol per mole of Arylketone, The amount of ammonium acetate used in the reaction is more preferably between 0.2-0.4.

The ratio of Arylketone:Acetic acid is maintained between 0.1-1.0, The ratio can be maintained as low as possible and is not very critical if the acetic acid is recovered and recycled to maintain the ratio of Arylketone to acetic acid between 0.2-0.7 for the generation of ammonium acetate during the reaction. The reaction temperature is maintained below 100° C., preferably the temperature is maintained between 80-90° C. The molar ratio of Arylketone to Cyanoacetic ester is maintained at 0.1-0.9, preferably 0.6-0.75.

According to another embodiment of the present invention, acetic acid is added portion wise to make up the losses.

In another embodiment of the present invention, the water of reaction can be distilled off together with acetic acid as an azeotrope at a reduced pressure of 100-600 mm of Hg A, preferably at 100-450 mm of Hg A during reaction.

In yet another embodiment, the recovered acetic acid can be either recycled to reaction vessel continuously after fractional distillation of acetic acid or used in next run without removal of water.

In another embodiment of the present invention, the reaction is carried out at temperature ranging from 70° C. to 100° C., preferably the reaction temperature ranges from 80-90° C., under reduced pressure preferably between 100-450 mm of Hg A.

The Cyanoacetic ester of Formula II can be prepared by using conventional methods known in the art.

The reaction is stopped when no significant drop in Arylketone is observed by Gas chromatographic analysis.

The inventors of the present invention have observed that keeping the reaction temperature below 100° C., in particular below 90° C., under reduced pressure, preferably 100-450 mm of Hg A with acetic acid as a solvent, lowers the generation of diaryl cyanoacrylamide. The process of the invention ensures the availability of acetic acid (which is made available by making up the losses of acetic acid as distillate, either by adding fresh acetic acid or by adding recycled acetic acid as such or after spot distillation) which lowers the chances of generation of Diaryl cyanoacrylamide and also simultaneously, generates the catalyst, ammonium acetate from liberated ammonia effectively.

Thus, for the manufacture of 2-Cyano-3,3-diarylacrylates of Formula I, according to the invention, it is necessary to maintain acetic acid level to such an extent that the ratio of Arylketone to acetic acid is always maintained between 0.2-0.7 and without using any other organic solvent. The invention also discloses a process for the manufacture of 2-Cyano-3,3-diarylacrylates maintaining temperature of reaction preferably below 90° C., under reduced pressure preferably between 100-450 mm of Hg A. Further, it has been found that it is not necessary to add catalyst in either higher molar ratio or in divided dosage, as the catalyst is continuously generated in the presence of acetic acid. Thus, it provides the added advantage of using lower mole of ammonium acetate and thus lowers the effluent generation.

In another embodiment, the invention relates to a composition comprising 2-Cyano-3,3-diarylacrylates of Formula I,

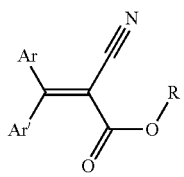

Formula I wherein, the composition of the product comprises 2-Cyano-3,3-diarylacrylate is in the range of about 98 to 99.5% and Diaryl cyanoacrylamide <0.2%.

The detail of the invention provided in the following example is given by the way of illustration only and should not be construed to limit the scope of the present invention.

EXAMPLES AND COMPARATIVE EXAMPLES

Comparative Example 1

Preparation of 2-Ethylhexyl-3,3-biphenyl cyanoacrylate according to U.S. Pat. No. 7,985,870

A 1000 mL four neck round bottom flask, equipped with a mechanical stirrer, a thermometer and a condenser, was charged with 2-ethylhexyl cyanoacetate (347 g, 1.76 gmol), benzophenone (200 g, 1.1 gmol), propanoic acid (165 g, 2.23 gmol) and ammonium acetate (31 g, 0.4 gmol). The stirred reaction mass was then heated to 85-90° C. Azeotrope of propanoic, acid/water mixture was distilled off over a period of 16 h under reduced pressure from 110-160 mm of Hg A (213-146 mbar) till the Gas chromatographic analysis showed no further significant decrease in benzophenone concentration in reaction mass. The loss of propanoic acid was continuously adjusted by adding the corresponding loss of propanoic acid every half an hour. The propanoic acid was then recovered under reduced pressure (20-40 mm of Hg A) at temperature 100-110° C. The HPLC analysis of reaction mass showed. Biphenyl cyanoacrylamide (BPCA) content of 1.2%. The crude reaction mixture was cooled and washed twice with 300 g portion of water and subsequently distilled to yield pale yellow colored viscous liquid (302 g, Yield 76%) which was found to be of 98.31% purity by Gas chromatographic analysis.

Experimental Example 1

Preparation of 2-Ethylhexyl-3,3-biphenylcyanoacrylate according to present invention in acetic acid and using ammonium acetate A 1000 mL four neck round bottom flask, equipped with a mechanical stirrer, a thermometer and a condenser, was charged with 2-ethylhexyl cyanoacetate (347 g, 1.76 gmol), benzophenone (200 g, 1.1 gmol), acetic acid (165 g, 2.75 gmol) and ammonium acetate (31 g, 0.4 gmol). The stirred reaction mass was then heated to 85-90° C. Azeotrope of acetic acid/water mixture was distilled off over a period of 16 h. under reduced pressure from 400-420 mm of Hg A till the Gas chromatographic analysis showed no further decrease in benzophenone concentration in reaction mass. The loss of acetic acid was continuously adjusted by adding the corresponding acetic acid. The acetic acid was then recovered under reduced pressure (30-60 mm of Hg A). The HPLC analysis of reaction mass showed BPCA content of 0.16%.

The crude reaction mixture was cooled and washed twice with 300 g portion of water and subsequently distilled to yield pale yellow colored viscous liquid of APHA<5.0 (301 g, Yield 75.8%) which was found to be of 99.46% purity by Gas chromatographic analysis.

Experimental Example 2

Preparation of 2-Ethylhexyl-3,3-biphenyl cyanoacrylate according to present invention in acetic acid and using ammonium acetate A 1000 mL four neck round bottom flask, equipped with a mechanical stirrer, a thermometer and a condenser was charged with 2-ethylhexyl cyanoacetate (236 g, 12 gmol), benzophenone (200 g, 1.1 gmol), acetic acid (165 g, 2.75 gmol) and ammonium acetate (34 g, 0.44 gmol). The stirred reaction mass was then heated to 85-90° C. Azeotrope of acetic acid/water mixture was distilled off over a period of 16 h under reduced pressure from 400-420 mm of Hg A, till the Gas chromatographic analysis showed no further significant decrease in benzophenone concentration in reaction mass. The loss of acetic acid was continuously adjusted by adding the corresponding acetic acid. The acetic acid was then recovered under reduced pressure of 30-60 mm of Hg A. The HPLC analysis of reaction mass showed BPCA content 0.18%. The crude reaction mixture was then cooled and washed twice with 300 g portion of water and subsequently distilled to yield pale yellow colored viscous liquid with APHA<7.0 (261 g, Yield 65.66%) which was found to be of 99.56% purity by Gas chromatographic analysis.

Experimental Example 3

Preparation of 2-Ethylhexyl-3,3-biphenylcyanoacrylate according to present invention using recovered acetic acid A 1000 mL four neck round bottom flask, equipped with a mechanical stirrer, a thermometer and a condenser, was charged with 2-ethylhexyl cyanoacetate (347 g, 1.76 gmol), benzophenone (200 g, 1.1 gmol), recovered acetic acid (168.3 g containing 2% water, 2.75 gmol) and ammonium acetate (31 g, 0.4 gmol). The stirred reaction mass was then heated to 85-90° C. Azeotrope of acetic acid/water mixture was distilled off over a period of 16 h. under reduced pressure from 400-420 mm of Hg A till the Gas chromatographic analysis showed no further decrease in benzophenone concentration in reaction mass. The loss of acetic acid was continuously adjusted by adding the corresponding recovered acetic acid. The acetic acid was then recovered under reduced pressure (30-60 mm of Hg A). The HPLC analysis of reaction mass showed BPCA content of 0.19%. The crude reaction mixture was cooled and washed twice with 300 g portion of water and subsequently distilled to yield pale yellow colored viscous liquid (303 g, Yield 76.3%) which was found to be of 99.48% purity by Gas chromatographic analysis.

Experimental Example 4

Preparation of Amyl-3,3-biphenylcyanoacrylate

A 1000 mL four neck round bottom flask, equipped with a mechanical stirrer, a thermometer and a condenser, was charged with amyl cyanoacetate (248 g, 1.6 gmol), benzophenone (182 g, 1.0 gmol), acetic acid (150 g, 2.5 gmol) and ammonium acetate (31 g, 0.4 gmol). The stirred reaction mass was then heated to 85-90° C. Azeotrope of acetic acid/water mixture was distilled off over a period of 16 h. under reduced pressure from 400-420 mm of Hg A till the Gas chromatographic analysis showed no further decrease in benzophenone concentration in reaction mass. The loss of acetic acid was continuously adjusted by adding the corresponding recovered acetic acid. The acetic acid was then recovered under reduced pressure (30-60 mm of Hg A). The HPLC analysis of reaction mass showed BPCA content of 0.17%. The crude reaction mixture was cooled and washed twice with 300 g portion of water and subsequently distilled to yield pale yellow colored viscous liquid (236.4 g, Yield 74.1%) which was found to be of 99.48% purity by Gas chromatographic analysis.

We claim:
1. A novel process for the preparation of 2-Cyano-3,3-diarylacrylates of Formula I

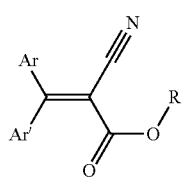

Formula I wherein,
Ar=Ar'=Phenyl or substituted phenyl
R=$C_1$-$C_{12}$ alkyl
comprising, reacting a Cyanoacetic ester of Formula II

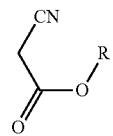

Formula II with an Arylketone of Formula III

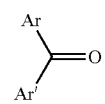

Formula III in the presence of an ammonium compound and acetic acid and without the use of organic solvent,
wherein the acetic acid is recovered with continuous distillation under reduced pressure, and
wherein the ammonium compound is ammonia or an ammonium salt.

2. The process for preparation of 2-Cyano-3,3-diarylacrylates according to claim 1, wherein the ammonium salt is ammonium acetate.

3. The process according to claim 1, wherein molar ratio of Arylketone to Cyanoacetic ester is 0.1-0.9.

4. The process according to claim 1 wherein the reaction is carried out between 70-100° C.

5. The process according to claim 1, wherein the reaction is carried out under reduced pressure from 100-600 mm Hg.

6. The process according to claim 1, wherein the ratio of Arylketone:Acetic acid is maintained between 0.1-1.0.

7. The process according to claim 2, wherein the ratio of Ammonium acetate:Arylketone is between 0.05-0.4.

8. The process according to claim 1, wherein the recovered acetic acid is recycled.

9. The process according to claim 1, wherein the Cyanoacetic ester is 2-Ethylhexyl cyanoacetate or amyl cyanoacetate and the Arylketone is Benzophenone.

10. The process according to claim 1, wherein molar ratio of Arylketone to Cyanoacetic ester is 0.6-0.75.

11. The process according to claim 1, wherein the reaction is carried out between 80-90° C.

12. The process according to claim 1, wherein the reaction is carried out under reduced pressure between 100-450 mm Hg.

13. The process according to claim 1, wherein the ratio of Arylketone:Acetic acid is maintained between 0.2-0.7.

14. The process according to claim 1, wherein the ratio of Ammonium acetate:Arylketone is between 0.2-0.4.

* * * * *